United States Patent
Dewdney et al.

(10) Patent No.: US 12,023,404 B2
(45) Date of Patent: Jul. 2, 2024

(54) PERSONAL CARE COMPOSITIONS

(71) Applicant: Colgate-Palmolive Company, New York, NY (US)

(72) Inventors: Nadine Dewdney, Union, NJ (US); Pooja Kulkarni, Plainsboro, NJ (US); Christine Boyke, Somerset, NJ (US); Ewelina Lesniak, Linden, NJ (US); Cheryl Kozubal, Somerset, NJ (US); Samuel Nyarko, Ewing, NJ (US); Brajesh Jha, Midlothian, VA (US)

(73) Assignee: Colgate-Palmolive Company, New York, NY (US)

(*) Notice: Subject to any disclaimer, the term of this patent is extended or adjusted under 35 U.S.C. 154(b) by 105 days.

(21) Appl. No.: 16/957,425

(22) PCT Filed: Dec. 13, 2018

(86) PCT No.: PCT/US2018/065336
§ 371 (c)(1),
(2) Date: Jun. 24, 2020

(87) PCT Pub. No.: WO2019/133268
PCT Pub. Date: Jul. 4, 2019

(65) Prior Publication Data
US 2020/0315947 A1    Oct. 8, 2020

Related U.S. Application Data

(60) Provisional application No. 62/612,328, filed on Dec. 30, 2017.

(51) Int. Cl.
| | | |
|---|---|---|
| *A61K 8/92* | (2006.01) | |
| *A61K 8/34* | (2006.01) | |
| *A61K 8/41* | (2006.01) | |
| *A61K 8/46* | (2006.01) | |
| *A61K 8/86* | (2006.01) | |
| *A61Q 19/10* | (2006.01) | |

(52) U.S. Cl.
CPC ............. *A61K 8/922* (2013.01); *A61K 8/345* (2013.01); *A61K 8/416* (2013.01); *A61K 8/463* (2013.01); *A61K 8/86* (2013.01); *A61Q 19/10* (2013.01); *A61K 2800/30* (2013.01); *A61K 2800/596* (2013.01)

(58) Field of Classification Search
CPC ........ A61Q 19/10; A61K 8/345; A61K 8/463; A61K 8/922; A61K 8/416; A61K 8/86; A61K 2800/30; A61K 2800/596
See application file for complete search history.

(56) References Cited

U.S. PATENT DOCUMENTS

| | | |
|---|---|---|
| 9,700,494 B2 | 7/2017 | Potechin |
| 9,820,924 B2 | 11/2017 | Pimenta |
| 2004/0166183 A1 | 8/2004 | Ruseler-van Embden et al. |
| 2010/0048706 A1 | 2/2010 | Subramanyam |
| 2011/0124542 A1* | 5/2011 | Sartingen ................. A61Q 5/02 510/130 |
| 2014/0186284 A1 | 7/2014 | Sha et al. |

FOREIGN PATENT DOCUMENTS

| | | |
|---|---|---|
| CN | 1527695 | 9/2004 |
| CN | 101878021 | 11/2010 |
| CN | 103038326 | 4/2013 |
| CN | 105848631 | 8/2016 |
| EP | 1275371 | 1/2003 |
| EP | 3087971 | 11/2016 |
| EP | 3251696 | 12/2017 |
| EP | 3348630 | 7/2018 |
| RU | 2505281 | 1/2014 |
| RU | 2633065 | 10/2017 |
| WO | 2009/073382 | 6/2009 |
| WO | 2012/021130 | 2/2012 |
| WO | WO 2014201541 | * 12/2014 |

OTHER PUBLICATIONS

International Search Report and Written Opinion of the International Searching Authority in International Application No. PCT/US2018/065336, mailed Mar. 25, 2019.

* cited by examiner

*Primary Examiner* — Lezah Roberts

(57) ABSTRACT

Disclosed herein are liquid cleansing compositions comprising a foam booster comprising ethoxylated hydrogenated castor oil present in an amount ranging from about 0.5% to about 2% based on the total weight of the composition, castor oil maleate, glycerin, and at least one surfactant, wherein the pH of the composition is less than about 7. The liquid cleansing compositions disclosed herein provide enhanced foam volume and texture. Further disclosed herein are methods of making a liquid cleansing composition.

15 Claims, No Drawings

PERSONAL CARE COMPOSITIONS

BACKGROUND

Liquid cleansing compositions, such as aqueous foaming compositions like hand soaps, body washes, and shower gels, should desirably have acceptable levels of foam production for consumer satisfaction. Foam production is a key attribute for consumers when choosing products. To achieve a desirable foam production, manufacturers incorporate sufficient quantities of active ingredients, such as surfactants, into the compositions.

Liquid cleansing compositions require minimal levels of surfactant to provide good cleaning and dispensing properties and good foaming of the liquid cleansing composition during use. Also, it is desired to provide a sufficient amount of foam that is stable for a desired amount of time during use and has a desirable foam texture, such as sufficient creaminess.

It is also desirable for liquid cleansing compositions to be physically stable at high and low temperatures and under typical aging conditions that may occur before and after the composition is purchased by a consumer. This means the compositions must meet consumer standards for clarity and viscosity and must show stability in the various thermal storage conditions that may be encountered during manufacture, transport, and supply. Therefore, it would be desirable to provide a liquid cleansing composition that is acceptable to the consumer, particularly with regard to foam production, viscosity, clarity, and stability.

Certain liquid cleansing compositions known in the art comprise maleated castor oil and a low pH preservative system comprising sodium benzoate and sodium salicylate. Such compositions, however, having a low pH preservative system, are known to have undesirable freeze-thaw issues, wherein precipitation may be evident after the composition has been subjected to low temperatures, such as −10° C. or −30° C. for at least one day.

BRIEF SUMMARY

Disclosed herein are liquid cleansing compositions comprising an ethoxylated hydrogenated castor oil such as PEG-60 hydrogenated castor oil. It has been discovered that the liquid cleansing compositions disclosed herein may reduce or eliminate precipitation occurring during a freezing and thawing process of the composition while enhancing the composition's foam appearance and performance.

Disclosed herein is liquid cleansing composition comprising a foam booster comprising ethoxylated hydrogenated castor oil present in an amount ranging from about 0.5% to about 2% based on the total weight of the composition, castor oil maleate, glycerin, and at least one surfactant, wherein the pH of the composition is less than about 7. In certain embodiments, the liquid cleansing composition has a viscosity ranging from about 1 to about 100 mPas (cps), such as from about 25 to about 35 mPas (cps) or about 30 mPas. In certain embodiments, the ethoxylated hydrogenated castor oil is PEG-60 hydrogenated castor oil, and in certain embodiments, the ethoxylated hydrogenated castor oil is present in an amount ranging from about 0.5% to about 1%, such as about 1%. In certain other embodiments, the liquid cleansing composition disclosed herein is substantially free of any additional foam booster. In certain embodiments the pH of the composition is about 5, and in certain embodiments, the compositions disclosed herein further comprise a fragrance, such as a fragrance present in an amount ranging from about 0.05% to 2%, such as about 0.25% to about 1%, or about 0.3%©, by weight relative to the total weight of the composition.

In various embodiments of the disclosure, the at least one surfactant is a salt of $C_{10}$-$C_{16}$ alcohol ethoxylate sulfate and a betaine. In certain embodiments, the salt of the $C_{10}$-$C_{16}$ alcohol ethoxylate sulfate comprises sodium lauryl ether sulfate, such as sodium lauryl ether sulfate with an average of 2 moles of ethylene oxide. In certain embodiments disclosed herein, the at least one surfactant comprises sodium lauryl ether sulfate and cocoamidopropyl betaine.

In certain embodiments, the liquid cleansing composition disclosed herein further comprises PEG-120 methyl glucose dioleate, and in certain embodiments the PEG-120 methyl glucose dioleate is present in an amount ranging from about 0.01% to about 0.5% by weight of the composition. In certain other embodiments, the liquid cleansing composition disclosed herein further comprises PEG-7 glyceryl cocoate. In certain embodiments, the castor oil maleate is present in an amount ranging from about 0.1% to about 1% by weight based on the total weight of the composition, and according to certain embodiments disclosed herein, the glycerin is present in an amount of about 3.4% by weight.

According to various embodiments disclosed herein, the liquid cleansing composition may be a body wash, a shower gel, or a hand soap, such as a foaming hand soap. In certain embodiments, the liquid cleansing composition disclosed herein remains clear after the composition has been frozen at −10 for at least one day, such as at least 3 days or at least 5 days, and then thawed, and in certain embodiments, the liquid cleansing composition remains clear after the composition has been frozen at −30° C. for at least one day, such as at least 3 days or at least 5 days, and then thawed.

Further disclosed herein is a method of making a liquid cleansing composition comprising mixing castor oil maleate and at least one fragrance to form a first mixture; mixing a foam booster comprising ethoxylated hydrogenated castor oil present in an amount ranging from about 0.5% to about 2% based on the total weight of the composition, glycerin, and at least one surfactant to form a second mixture; combining the first mixture and the second mixture to form a liquid cleansing composition; and adjusting the pH of the composition to less than about 7.

According to certain embodiments of the methods disclosed herein, the at least one fragrance is present in an amount of about 1% by weight based on the total weight of the liquid cleansing composition. In certain embodiments of the methods disclosed herein, the ethoxylated hydrogenated castor oil is PEG-60 hydrogenated castor oil, and in certain embodiments, the ethoxylated hydrogenated castor oil is present in an amount ranging from about 0.5% to about 1% by weight based on the total weight of the composition. According to various embodiments of the disclosure, the pH may be adjusted with citric acid, and in certain embodiments the pH may be adjusted to about 5.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiments is merely exemplary in nature and is in no way intended to limit the invention, its application, or uses.

As used throughout; ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

As used herein, the term "one or more of" with respect to a listing of items such as, for example, A and B, means A alone, B alone, or A and B. The term "at least one of" is used to mean one or more of the listed items can be selected.

Unless otherwise specified, all percentages and amounts expressed herein and elsewhere in the specification should be understood to refer to percentages by weight. The amounts given are based on the active weight of the material.

Disclosed herein are liquid cleansing compositions comprising a foam booster comprising ethoxylated hydrogenated castor oil. As used herein, the term "foam booster" indicates a substance that increases the amount of foam (e.g., the foam volume) the composition produces. A foam booster may also enhance the quality and texture of the foam, such as by decreasing the average radius of the foam bubbles and making the foam creamier, thicker, more stable, and/or longer-lasting. In certain embodiments, the compositions disclosed herein are substantially free of any additional foam booster other than an ethoxylated hydrogenated castor oil. As used herein, "substantially free" indicates that the composition comprises no effective amount of the material, such as the additional foam booster.

Ethoxylated Hydrogenated Castor Oil

The ethoxylated hydrogenated castor oils used in the compositions disclosed herein may be prepared by hydrogenating castor oil and treating the hydrogenated product with from about 10 to about 200 moles of ethylene glycol. These ethoxylated hydrogenated castor oils are known by the non-proprietary name of PEG hydrogenated castor oils, in accordance with dictionary of the Cosmetics, Toiletries and Fragrance Association, 3rd Edition which name is used in conjunction with a numeric suffix to designate the degree of ethoxylation of the hydrogenated castor oil product, i.e., the number of moles of ethylene oxide added to the hydrogenated castor oil product. Suitable PEG hydrogenated castor oils include, for example, PEG 16, 20, 25, 30, 40, 50, 60, 80, 100, and 200. In certain embodiments, the ethoxylated hydrogenated castor oil is PEG-60 hydrogenated castor oil, such as Cremaphor® RH 60, a commercially available product from BASF-Wyandotte, Parsippany, N.J.

Ethoxylated hydrogenated castor oil may be present in the compositions disclosed herein in any amount effective to produce the desired foaming characteristics of the composition. For example, in certain embodiments, the ethoxylated hydrogenated castor oil may be present in the composition in an amount ranging from about 0.1% to about 2%, such as from about 0.5% to about 1.5%, by weight based on the total weight of the composition. In certain embodiments disclosed herein, the ethoxylated hydrogenated castor oil may be present in the composition in an amount of about 0.5% by weight of the composition, and in certain embodiments, the ethoxylated hydrogenated castor oil may be present in the composition in an amount of about 1% by weight of the composition. In certain embodiments, the ethoxylated hydrogenated castor oil is PEG-60 hydrogenated castor oil present in an amount of about 1% by weight based on the total weight of the composition, Castor Oil Maleate The liquid cleansing compositions disclosed herein further comprise castor oil maleate (castoryl maleate). In certain embodiments, castor oil maleate may be present in the composition in an amount ranging from about 0.1% to about 1% by weight of the composition, such as from about 0.3% to about 0.5% by weight. In other embodiments, the castor oil maleate may be present in the composition in an amount of about 0.3% by weight or about 0.5% by weight. Castor oil maleate is available as Ceraphyl® RMP from ISP Corp, Glycerin In another embodiment, glycerin may be included in the liquid cleansing compositions disclosed herein. The glycerin may be of any origin, such as, for example, of animal origin or of vegetable origin. In certain embodiments, glycerin may be present in the compositions disclosed herein in an amount that is greater than the castor oil maleate. In certain embodiments wherein the composition further comprises PEG-7 glyceryl cocoate and/or PEG-6 caprylic/capric glycerides, glycerin may be present in the composition in an amount that is greater than any or all of the castor oil maleate, the PEG-7 glyceryl cocoate and/or the PEG-6 caprylic/capric glycerides. Glycerin can be included in any desired amount to provide a desired level of moisturization. In one embodiment, the glycerin is present in an amount ranging from about 1% to about 8% by weight based on the total weight of the composition, in other embodiments, the glycerin can be present in an amount of about 1%, about 1.5%, about 2%, about 2.5%, about 3%, about 3.4%, about 3.5%, about 4%, about 4.5%, about 5%, about 5.5%, about 6%, about 6.5%, about 7%, or about 7.5% by weight based on the total weight of the composition.

Surfactants

The liquid cleansing compositions disclosed herein also comprise at least one surfactant, such as anionic, nonionic, cationic, amphoteric, and/or zwitterionic surfactants.

A variety of anionic surfactants can be utilized in the liquid cleansing composition including, for example, long chain alkyl ($C_6$-$C_{22}$) materials such as long chain alkyl sulfates, long chain alkyl sulfonates, long chain alkyl phosphates, long chain alkyl ether sulfates, long chain alkyl alpha olefin sulfonates, long chain alkyl taurates, long chain alkyl isethionates (SCI), long chain alkyl glyceryl ether sulfonates (AGES), sulfosuccinates and the like. These anionic surfactants can be alkoxylated, for example, ethoxylated, although alkoxylation is not required. These surfactants are typically highly water soluble as their sodium, potassium, alkyl and ammonium or alkanol ammonium contain salt form and can provide high foaming cleansing power. Other equivalent anionic surfactants may be used. In one embodiment, the anionic surfactant comprises sodium laureth sulfate, sodium pareth sulfate, or combinations thereof. Anionic surfactants can be included in any desired amount. In certain embodiments, the liquid cleansing composition comprises an anionic surfactant in an amount ranging from about 5% to about 20%, such as from about 10% to about 15%, by weight based on the total weight of the composition.

Amphoteric surfactants may also be included in the liquid cleansing compositions disclosed herein. These amphoteric surfactants are typically characterized by a combination of high surfactant activity, lather forming, and mildness. Amphoteric surfactants include, but are not limited to, derivatives of aliphatic secondary and tertiary amines in which the aliphatic radical can be straight chain or branched and wherein one of the aliphatic substituents contains about 8 to about 18 carbon atoms and one contains an anionic water solubilizing group. e.g., carboxy, sulfonate, sulfate, phosphate, or phosphonate. Examples of such compounds include sodium 3-dodecyaminopropionate, sodium 3-dodecylaminopropane sulfonate, N-alkyl taurines and N-higher alkyl aspartic acids. Other equivalent amphoteric surfactants may be used. Examples of amphoteric surfactants include, but are not limited to a range of betaines including, for example, high alkyl betaines, such as coco dimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl)carboxymethyl betaine, oleyl dimethyl gamma-carboxypropyl betaine, and lauryl bis-(2-hydroxypropyl)alpha-carboxyethyl betaine, sulfobetaines such as coco dimethyl sulfopropyl betaine, stearyl dimethyl sulfopropyl betaine, amido betaines, amidosulfobetaines and the like. Betaines having a long chain alkyl group, particularly coco, may also be used, as are those that include an amido groups such as the cocoamidopropyl and cocoamidoethyl betaines. Amphoteric surfactants can be included in any desired amount. In one embodiment, amphoteric surfactants are present in the liquid cleansing composition in an amount ranging from about 1% to about 15%, such as about 4% to about 6?, by weight based on the total weight of the composition.

Nonionic surfactants that may be present in the compositions include the primary aliphatic alcohol ethoxylates, secondary aliphatic alcohol ethoxylates, alkylphenol ethoxylates, and condensates of ethylene oxide with sorbitan fatty acid esters such as the Tween® surfactants. Other suitable water-soluble nonionic surfactants are marketed under the trade name Pluronic®. The compounds are formed by condensing ethylene oxide with a hydrophobic base formed by the condensation of propylene oxide with propylene glycol.

Preservatives

The liquid cleansing compositions disclosed herein can also contain a preservative, such as a preservative or combination of preservatives in an amount ranging from about 0.01 to about 5%, such as about 0.01 to about 1%, by weight based on the total weight of the composition. As used herein, the term "preservative" refers to a compound or compounds for the prevention or retardation of the growth of microorganisms in the composition, thereby preventing or retarding deterioration of the composition due to microorganisms. Examples of preservatives include, but are not limited to, sorhic acid, potassium sorbate, the parabens (like benzylparaben), imidazolinylurea, methylchloroisothiazolinone, and the hydantoins, like DMDM hydantoin. Additional preservatives as disclosed in the CTFA Handbook at page 78.

In certain embodiments, the preservative may be chosen from salicylate salts and benzoate salts. In one exemplary embodiment, the preservative comprises a salicylate salt and a benzoate salt, such as sodium salicylate and sodium benzoate or potassium salicylate and potassium benzoate. In some embodiments, the total amount of the salicylate salt and the benzoate salt may range from about 0.25% to about 1%, such as 0.4%, about 0.5%, or about 0.6% by weight based on total weight of the composition.

In certain embodiments, PEG-7 glyceryl cocoate may be present in the liquid cleansing compositions disclosed herein, for example in an amount ranging from about 0.01% to about 0.5% by weight of the composition, such as about 0.01% or about 0.2% by weight. PEG-7 glyceryl cocoate is available from Henkel KGaA as Cetiol®.

In certain embodiments, the liquid cleansing compositions disclosed herein may further comprise PEG-6 caprylic/capric glycerides, and in certain embodiments, the liquid cleansing compositions disclosed herein may be substantially free of PEG-6 caprylic/capric glycerides. When included in the compositions disclosed herein, PEG-6 caprylic/capric glycerides may be present in the composition in an amount ranging from about 0.05% to about 1% by weight of the composition. In one embodiment, the amount is about 0.5% by weight, and in one embodiment, the composition is substantially free of PEG-6 caprylic/capric glycerides. PEG-6 caprylic/capric glycerides is available from Croda as Glycerox™ 767.

Optionally, the liquid cleansing compositions disclosed herein may comprise PEG-120 methyl glucose dioleate. In certain embodiments, the amount of PEG-120 methyl glucose dioleate may range from about 0.01% to about 0.5% by weight of the composition, such as about 0.15% by weight. PEG-120 methyl glucose dioleate is available from Lubrizol Advanced Materials as Glucamate® DOE-120 thickener. The inclusion of PEG-120 methyl glucose dioleate may, in certain embodiments, further increase the foam stand up and skin feel properties.

The liquid cleansing compositions disclosed herein may comprise water. Water can be present in any desired amount of the cleansing composition to form a typical cleansing composition, such as a shower gel, a body wash, or a liquid hand soap. In certain embodiments, the compositions disclosed herein comprise at least about 50% water, such as at least about 60% water, or at least about 70% water.

Additional Ingredients

The compositions disclosed herein may further comprise optional additional ingredients, such as those yell-known to persons of ordinary skill in the art of liquid cleansing compositions. Additional optional ingredients may be included to provide added functional effect or to make the compositions more attractive. In certain embodiments, the compositions disclosed herein may include, for example, additional surfactants, hydrotopes, viscosity modifiers, stabilizers, enzymes, disinfectants, antioxidants, chelating agents, antibacterial agents/preservatives, optical brighteners, opacifiers, pigments, dyes, colorants, perfumes, fragrances, and mixtures thereof. In certain exemplary embodiments, the liquid cleansing compositions disclosed herein further comprise at least one fragrance. In certain embodiments, the at least one fragrance may be present in any amount sufficient to impart the desired fragrance to the composition, such as, for example, an amount ranging from about 0.05% to 2%, such as from about 0.1% to about 1%, or from about 0.25% to about 3%, by weight based on the total weight of the composition.

In certain embodiments, the cleansing compositions disclosed herein may comprise a thickener. Examples of thickeners that may be used include, but are not limited to, xanthan gum, konjac mannan, gellan gum, carrageenan, carboxymethyl cellulose, guar gum, rhamsan gum, furcellaran gum, celluloses, polysaccharides, pectin, alginate, and arabinogalactan. In certain embodiments, the thickener is present in an amount alone or in combination ranging from about 0.1% to about 5% by weight, such as about 0.25% to about 2% by weight, about 0.75% to about 1.5% by weight, or about 1% to about 1.25% by weight based on the total weight of the composition.

In another embodiment, the compositions can be opacified by including an opacifier, such as sunflower oil or Euperlan® Green opacifier from Cognis (55-65% water, 15-25% lauryl glucoside, and 15-25% stearyl citrate). The opacifier can be present in an amount ranging from about 1% to about 5% by weight of the composition. In certain embodiments, sunflower oil or Euperlan® Green may be present in an amount ranging from about 1% to about 5%, such as from about 2% to about 4% by weight of the composition. In certain embodiments, the opacifier is present in the composition in an amount of about 3% by weight of the composition.

The liquid cleansing compositions disclosed herein can, in certain embodiments, contain an antioxidant and/or an ultra-violet light (UV) absorber, each of which may be independently present in an amount ranging from about 0.01% to about 0.5%, by weight based on the total weight of the composition. Examples of antioxidants and UV absorbers include, but are not limited to, BHA, BHT, sodium ascorbate, potassium sulfite, erythorbic acid, benzophenone-1 through benzophenone-12, and PABA. Additional antioxidants and UV absorbers can be found in the CTFA Handbook at pages 78 and 98.

In certain embodiments, the cleansing composition can contain a chelator. Examples of a chelator include, but are not limited to sodium phytate and tetrasodium EDTA. In certain embodiments, the chelator is present in an amount ranging from about 0.001% to about 3% by weight, such as about 0.01% to about 1.5% by weight, about 0.05% to about 1.0% by weight, or about 0.26% by weight of the composition.

In certain embodiments disclosed herein, the composition may further comprise flaxseed extract, which includes proteins, omega-3 fatty acids, and omega-6 fatty acids. Flaxseed extract is available from Natunola Health, Inc. as Natunolata™ Flax Protein. In certain embodiments, the amount of the flaxseed extract may range from about 0.3% to about 1% by, weight based on the total weight of the composition. In one embodiment, the amount of flaxseed extract in the composition may range from about 0.5% to about 15% by weight. In other embodiments, the amount is about 1%, about 2%, about 3%, about 4%, about 5%, or at least about 0.5% by weight. In other embodiments, the amount is less than about 10%, less than about 5%, less than about 3'%©, or less than about 2% by weight.

The compositions disclosed herein may optionally further comprise one or more additional viscosity modifiers or control agents. Such agents include, but are not limited to, polypropylene glycol, linear $C_1$-$C_5$ alcohols such as ethanol, polysorbate 2.0 (Tween® 20), polyethylene oxide-polypropylene block copolymers (such as Pluronic® L44, Pluronic® L35, or Pluronic® L31 poloxamers), polyethylene glycol 55 (PEG-55), glycerin, diethylene glycol, Glucam® P-10 propylene glycol ether of methyl glucose with 10 polypropylene oxide units, Pluriol® E300 alkoxylates based on ethylene oxide and propylene oxide, sodium cumene sulfonate (SCS), sodium xylene sulfonate (SXS), Glucam® P-20 propylene glycol ether of methyl glucose with 20 polypropylene oxide units, Glucam® E-20 ethylene glycol ether of methyl glucose with 20 polyethylene oxide units, Glucam® E-10 ethylene glycol ether of methyl glucose with 10 polyethylene oxide units, and short chain ethoxylated propoxylated alcohols such as PPG2-Buteth-3, PPG3-Buteth-5, or PPG5-Buteth-7.

The compositions disclosed herein may further comprise one or more ionic additives as viscosity modifiers. The ionic additive may be a salt, which can include any desirable salt. Examples of salts include, but are not limited to, sodium chloride and magnesium sulfate.

The compositions disclosed herein may, in certain embodiments, include an antimicrobial. Examples of antimicrobials are 2-hydroxy-4,2'4' trichlorodiphenylether (DP300), lactic acid, quaternary ammonium compounds such as Triclosan (2,4,4'-trichloro-2'-hydroxydiphenyl ether), DMDM hydantoin, formaldehyde and/or imidazolidinyl urea, and/or their equivalents, and the like. In certain embodiments, an antimicrobial may be present in the composition in an amount ranging from about 0.0001% to about 2%, by weight based on the total weight of the composition.

In certain embodiments, the composition is substantially free of inorganic salts, such as sodium chloride. In certain other embodiments, the amount of sodium chloride (and/or all inorganic salts) in the composition is limited to 1% by weight or less.

In certain embodiments, the liquid cleansing compositions disclosed herein may comprise an additional foam booster, such as an alkanol amide to provide foam enhancement. Additional foam boosters can be chosen from, but are not limited to, cocamide MEA, cocamide DEA, soyatnide DEA, lauramide DEA, oleamide IPA, stearamide MEA, myristamide DEA, lauramide MEA, capramide DEA, ricinoleamide DEA, myristamide DEA, stearamide DEA, oleylamide DEA, tallowamide DEA, lauramide IPA, tallowamide MEA, isostearamide DEA, isostearamide MEA, and mixtures thereof. According to certain embodiments of the disclosure, the liquid cleansing composition may be substantially free of an additional foam booster.

Skin Conditioners and Moisturizers

In another embodiment, the liquid cleansing compositions disclosed herein can contain various skin conditioning agents and moisturizing agents. In one embodiment, the composition may contain vitamin E and/or vitamin E acetate (a vitamin E precursor). In one embodiment, the amount of vitamin E and/or vitamin E acetate in the composition may range from about 0.005% to about 0.5% by weight based on the total weight of the composition. In other embodiments, vitamin E may be present in an amount of at least about 0.01%, at least about 0.05%, or at least about 0.1%, by weight based on the total weight of the composition. In other embodiments, vitamin E may be present in an amount of less than about 0.5%, by weight based on the total weight of the composition.

In another embodiment, the liquid cleansing composition disclosed herein may also contain creatine. Creatine can, for example, be used to support the energy cycle in skin cells. Creatine can be included at any desired amount to achieve any desired level of energy support in cells, in one embodiment, the creatine is present in the composition in an amount ranging from about 0.1% to about 2%, by weight based on the total weight of the composition.

In another embodiment, the composition can further include a moisturizing agent, for example a moisturizing agent chosen from a hydrolyzed keratin, hydroxyethyl urea, and/or a quaternized nitrogen moisturizing agent. Any one of these can be used alone, or any combination of these materials can be used.

In another embodiment, a hydrolyzed keratin can be present in the liquid cleansing compositions disclosed herein. Any hydrolyzed keratin can be included in the composition. In one embodiment, the hydrolyzed keratin comprises an extract of goat hair. In one embodiment, the goat hair is cashmere. The hydrolyzed keratin can be present in the composition in any desired amount to give a desired level of moisturization. In one embodiment, the hydrolyzed keratin is present in an amount ranging from about 0.0001% to about 0.005%, such as from about 0.0005% to about 0.005%, or 0.0015% by weight based on the total weight of the composition.

In another embodiment, hydroxyethyl urea can be present in the liquid cleansing compositions disclosed herein. The hydroxyethyl urea can be present in the composition in any desired amount to give a desired level of moisturization. In one embodiment, the hydroxyethyl urea is present in an amount ranging from about 1% to about 13%, such as about 6%, by weight based on the total weight of the composition.

In another embodiment, a quaternary nitrogen moisturizing agent can be present in the liquid cleansing compositions disclosed herein. The quaternary nitrogen moisturizing agent is a moisturizing agent that contains a quaternary nitrogen in its structure. Examples of quaternary nitrogen moisturizing agents include, but are not limited to, hydroxypropyl bis-hydroxyethyldimonium chloride (available as Cola® Moist 200 from Colonial Chemicals. Inc.), a choline salt, carnitine, and combinations thereof. Naturally occurring carnitine is L-carnitine. The quaternary nitrogen moisturizing agent can be present in the composition in any desired amount to give a desired level of moisturization. In one embodiment, the quaternary nitrogen moisturizing agent may be present in an amount ranging from about 0.1% to about 5%, such as from about 0.1% to about 1%, or about 1%, by weight based on the total weight of the composition.

In another embodiment, skin compatible oils can be included in the liquid cleansing compositions disclosed herein. Skin compatible oils may include a range of liquid hydrocarbons, for example, linear and branched oils such as liquid paraffin, squalene, squalene, mineral oil, low viscosity synthetic hydrocarbons such as polyalphaolefins, commercially available from ExxonMobil under the trade name Puresyn® and polybutene under the trade name Panalane® or Indopol® Light (low viscosity) highly branched hydrocarbon oils may also be suitable in some instances. Other useful skin compatible oils may be silicone based, for example, linear and cyclic polydimethyl siloxane, organo functional silicones (alkyl and alkyl aryl), and amino silicones.

In another embodiment, the liquid cleansing compositions disclosed herein can contain suspended material. The suspended material can, for example, be in the form of beads. In one embodiment, the beads are available from ISP Corp. as Captivates® HC4567, HC4451, HC4590, HC, 4635, HC4637, or HC4638.

Characteristics

The liquid cleansing compositions disclosed herein comprising an ethoxylated hydrogenated castor oil may exhibit enhanced foaming properties as compared to comparable liquid cleansing compositions that do not contain an ethoxylated hydrogenated castor oil. As used herein, the phrase "foaming properties" refers to, for example, flash foam and foam volume, which are among the main factors affecting the consumer perception about the foam quality. Well-known tests, notably as described in the Examples below, may be used to measure these factors. The flash foam, as used herein, is a measure of the quickness of foam generation. In certain embodiments, flash foam may be read after a certain number of rotations of the composition in a container, such as an enclosed cylinder, wherein 1 rotation is equal to one upside down/right side up motion of the cylinder. The foam volume test is an inverted cylinder test in which a volume of the composition (which may be optionally diluted with water) is placed in a stoppered graduated cylinder (such as a 500 mL or a 100 mL graduated cylinder) and inverted multiple cycles at a given rate, such as 40 cycles at 30 cycles/minute. After the inversions, the foam height in the graduated cylinder may be measured. In certain embodiments, the compositions disclosed herein can achieve a foam volume ranging from about 80 mL to about 120 mL, such as about 85 mL to about 95 mL, or greater than about 90 mL.

In certain compositions known in the art, such as compositions having a low pH, certain additives, such as, for example, fragrances, may become insoluble, such as during freeze/thaw stability testing. In certain embodiments disclosed herein, additives such as fragrances may remain soluble in a composition comprising an ethoxylated hydrogenated castor oil, such as PEG-60 hydrogenated castor oil, having a low pH, such a pH less than about 7 or a pH of about 5. In certain embodiments disclosed herein, the ratio of fragrance to ethoxylated hydrogenated castor oil present in the composition may be about 1:4, such as about 1:2, about 1:1, or about 2:1. For example, in certain embodiments, the fragrance may be present in an amount of about 025% by weight and the ethoxylated hydrogenated castor oil may be present in an amount of about 0.5% by weight or about 1% by weight. In certain other embodiments, the fragrance may be present in an amount of about 1% by weight and the ethoxylated hydrogenated castor oil may be present in an amount of about 0.5% by weight or about 1% by weight.

In certain embodiments disclosed herein, the ethoxylated hydrogenated castor oil improves freeze/thaw stability and also may have the additional benefit of improved foam texture. With the addition of ethoxylated hydrogenated castor oil, the foam texture may, in certain embodiments, become thicker, creamier, more stabile, and/or longer lasting. In certain embodiments, the foam structure also provides tighter, smaller foam bubbles. For example, in certain embodiments of the compositions disclosed herein, the foam may comprise bubbles having an initial radius of less than about 65 μm, such as, for example, less than about 62 μm or about 61 μm. In certain embodiments, the foam may comprise bubbles having a final radius, such as a radius after 120 seconds, of less than about 95 μm, such as, for example, less than about 90 μm or about 85 μm, Bubble radius may be measured, for example, on a Kruss Dynamic Foam Analyzer. In certain embodiments, an initial bubble radius may be measured at the end of foaming, such as after about 20 seconds, and in certain embodiments, the final bubble radius may be measured at any point in time after the initial bubble radius is measured, such as, for example, after about 60 seconds, about 120 seconds, or about 180 seconds.

The viscosity of the liquid cleansing compositions disclosed herein may range from about 1 to about 100 mPas (cps), such as from about 5 to about 30 mPas, or about 30 mPas, as measured on a Brookfield viscometer with spindle 3 at 100 rpm at 25° C. for 1 minute. In certain embodiments, the viscosity allows the composition to be poured from a container, and in certain embodiments, the viscosity allows the composition to be dispensed through a foaming dispenser and generate a foam. A foaming dispenser is any dispenser that intakes a liquid composition and then dispenses the composition as a foam.

In some embodiments the pH of the liquid cleansing compositions disclosed herein ranges from about 2 to about 9, such as about 3 to about 7 or from about 4 to about 6, such as about 5. The pH may be measured at 25° C. The pH can be adjusted by any material known to alter the pH, such a material that reduces the pH to less than about 7. In one embodiment, an organic acid is used to adjust the pH. Examples of organic acids include, but are not limited to, alpha-hydroxy acids, lactic acid, citric acid, salicylic acid, glycolic acid, ortho hydroxyl benzoic acid, and combinations thereof. In another embodiment, an inorganic acid is used to adjust the pit. As a non-limiting example, the inorganic acid is sulphuric acid. Also, combinations of organic and inorganic acids can be used. The amount of material that reduces the pH can be any, amount such that the desired pH is achieved in the cleaning composition. In one embodiment when an organic acid is used, the organic acid can be present in an amount ranging from about 0.01% to about 2.5%, such as about 0.1% to about 0.6%, or about 0.3% to 0.55%, or about 0.35% to about 0.5%, by weight of the composition, to act as a pH adjuster for the composition.

The liquid cleansing compositions disclosed herein may be made by mixing of the materials. Certain embodiments disclosed herein include a method of making a liquid cleansing composition comprising mixing castor oil maleate and at least one fragrance to form a first mixture; mixing a foam booster comprising ethoxylated hydrogenated castor oil present in an amount ranging from about 0.5% to about 2% based on the total weight of the composition, glycerin, and at least one surfactant to form a second mixture; and combining the first mixture and the second mixture to form a liquid cleansing composition.

Also disclosed herein is a method of cleansing the skin, hair and/or nails comprising applying the liquid cleansing composition disclosed herein to the skin, hair, or nails; washing; and optionally rinsing with water. In addition to cleansing, the compositions disclosed herein can be used to moisturize skin, hair, and/or nails. For example, in certain embodiments the liquid cleansing composition may be applied to skin, hair, and/or nails. If the composition is a rinse-off composition; the composition is rinsed off. In certain embodiments, the composition can be left on for any desired amount of time. The composition can be in the form of a body wash, a shower gel, a hand soap, a shampoo, a conditioner, a dishwashing liquid; a skin lotion, a sunscreen, or a bubble bath or the like.

EXAMPLES

Example 1

Aqueous foamable compositions were prepared containing varying amounts of PEG-60 hydrogenated castor oil. The compositions prepared are shown below in Table 1, where each cell indicates the % by weight of the ingredients; compared to the total weight of the composition.

TABLE 1

| Aqueous foamable compositions | | | |
|---|---|---|---|
| Ingredient | Composition A | Composition B | Composition C |
| Water, fragrances, and colorants | QS | QS | QS |
| Sodium laureth sulfate | 15.23 | 15.23 | 15.23 |
| Cocoamidopropyl betaine | 6 | 6 | 6 |
| 99.0%-101.0% Glycerin USP | 3.43 | 3.43 | 3.43 |
| Tetrasodium EDTA - 39% solution | 0.26 | 0.26 | 0.26 |
| Maleated castor oil | 0.3 | 0.3 | 0.3 |
| PEG-7 glyceryl cocoate | 0.2 | 0.2 | 0.2 |
| PEG-120 methyl glucose dioleate | 0.15 | 0.15 | 0.15 |
| Citric acid - 50% food grade | 0.3 | 0.3 | 0.3 |
| Sodium benzoate | 0.29 | 0.29 | 0.29 |
| Sodium salicylate | 0.31 | 0.31 | 0.31 |
| PEG-60 hydrogenated castor oil | 0 | 0.5 | 1.0 |
| Average foam volume (mL) | 86.35 ± 0.92 | 85.50 ± 1.98 | 96.40 ± 5.94 |

TABLE 1-continued

| Aqueous foamable compositions | | | |
|---|---|---|---|
| Ingredient | Composition A | Composition B | Composition C |
| Flash foam | similar | similar | relatively quick |
| Bubble radius | similar | similar | relatively small |

As demonstrated by Table 1, Composition C, comprising 1% PEG-60 hydrogenated castor oil, had a significantly higher foam volume, with both a quicker flash foam and a smaller bubble radius than Composition A and B, comprising either no or 0.5% PEG-60 hydrogenated castor oil, respectively.

Example 2

The bubble radius for the three sample compositions of body wash was measured using a Dynamic Foam Analyzer. An initial bubble radius was measured at the end of foam (i.e., after about 20 seconds). A final bubble radius was measured after approximately 120 seconds. As shown in Table 2 below, both the initial and final average bubble radius was smaller with the addition of 1% by weight of PEG-60 hydrogenated castor oil to the composition compared to both a composition not containing PEG-60 hydrogenated castor oil and a composition comprising 0.5% by weight PEG-60 hydrogenated castor oil.

TABLE 2

| Average bubble radius of compositions comprising PEG-60 hydrogenated castor oil | | | | |
|---|---|---|---|---|
| % PEG-60 hydrogenated castor oil in composition | Average initial radius (μm) | Standard Deviation | Average final radius (μm) | Standard Deviation |
| 0% | 63 | 0 | 90 | 1.414 |
| 0.5% | 64.5 | 2.121 | 92 | 2.828 |
| 1% | 60.5 | 0.707 | 85 | 2.828 |

Example 3

The quantities of sodium laureth sulfate, cocoamidopropyl betaine, maleated castor oil, glycerin, and PEG-60 hydrogenated castor oil were varied in the preparation of 17 different liquid cleansing composition samples. To assess the impact of variability in concentration of the five materials on the final product characteristics, materials were varied within a +/−10% range, as shown below in Table 3.

TABLE 3

| % by weight of 5 variables in sample liquid cleansing compositions | | | | | |
|---|---|---|---|---|---|
| Samples | PEG-60 hydrogenated castor oil (%) | Sodium laureth sulfate (%) | CAP betaine (%) | Maleated castor oil (%) | Glycerin (%) |
| 1 | 0.55 | 11.95 | 5.4 | 0.27 | 3.77 |
| 2 | 0.55 | 11.95 | 6.6 | 0.33 | 3.77 |
| 3 | 0.45 | 9.78 | 5.4 | 0.33 | 3.08 |
| 4 | 0.45 | 11.95 | 6.6 | 0.27 | 3.77 |
| 5 | 0.45 | 11.95 | 6.6 | 0.33 | 3.08 |
| 6 | 0.45 | 9.78 | 6.6 | 0.33 | 3.77 |
| 7 | 0.55 | 9.78 | 6.6 | 0.33 | 3.08 |
| 8 | 0.45 | 11.95 | 5.4 | 0.27 | 3.08 |

TABLE 3-continued

% by weight of 5 variables in sample liquid cleansing compositions

| Samples | PEG-60 hydrogenated castor oil (%) | Sodium laureth sulfate (%) | CAP betaine (%) | Maleated castor oil (%) | Glycerin (%) |
|---|---|---|---|---|---|
| 9 | 0.55 | 9.78 | 6.6 | 0.27 | 3.77 |
| 10 | 0.45 | 9.78 | 5.4 | 0.27 | 3.77 |
| 11 | 0.45 | 11.95 | 5.4 | 0.33 | 3.77 |
| 12 | 0.55 | 11.95 | 6.6 | 0.27 | 3.08 |
| 13 | 0.55 | 11.95 | 5.4 | 0.33 | 3.08 |
| 14 | 0.55 | 9.78 | 5.4 | 0.27 | 3.08 |
| 15 | 0.45 | 9.78 | 6.6 | 0.27 | 3.08 |
| 16 | 0.5 | 10.87 | 6.0 | 0.30 | 3.43 |
| 17 | 0.55 | 9.78 | 5.4 | 0.33 | 3.77 |

All of the 17 prepared compositions contained similar amounts of additional ingredients, as shown below in Table 4.

TABLE 4

% by weight of ingredients in sample compositions

| Ingredient | % by weight in Compositions 1-17 |
|---|---|
| Water, colorants, and fragrances | QS |
| Sodium laureth sulfate | 9.78-11.95 |
| CAP betaine | 5.4-6.6 |
| Glycerin | 3.08-3.77 |
| PEG-60 hydrogenated castor oil | 0.45-0.55 |
| Tetrasodium EDTA | 0.05-0.5 (e.g., 0.26 or 0.1) |
| Maleated castor oil | 0.27-0.33 |
| PEG-7 glyceryl cocoate | 0.20 |
| PEG-120 methyl glucose dioleate | 0.15 |
| Citric acid | 0.55 |
| Sodium benzoate | 0.05-0.5 (e.g., 0.29) |
| Sodium salicylate | 0.05-0.5 (e.g., 0.31) |

The material variables were selected based, for example, on the amounts in which they are present in the composition by weight and the likelihood of impacting the responses. The following responses were measured: pH, viscosity, and appearance after freeze/thaw.

The order of addition of the materials was as follows: water, sodium laureth sulfate, sodium benzoate, sodium salicylate, cocoamidopropyl betaine, PEG-60 hydrogenated castor oil, PEG-120 methyl glucose dioleate, EDTA, PEG-7 glyceryl cocoate, glycerin, and pre-mixed maleated castor oil/fragrance. The pH and viscosity were measured after the addition of the above-listed ingredients, and then adjustments were made with the 50% citric acid solution to meet the target pH of 5.0. The samples were then aged under various freeze/thaw conditions and assessed.

Aging conditions consisted of samples being stored at −10° C. and −30° C. for 1, 3, and 5 days. The samples were also subjected to a slow thaw process wherein samples were placed in the −30° C., −10° C., and 4° C., freezers for subsequent 2 day periods, culminating in a complete thaw at 25° C. The results of the pH responses are shown below in Table 5, and the results of the viscosity responses are shown in Table 6 below, where each cell in Table 6 represents cps units (mPa/s). Viscosity was measured on a Brookfield viscometer with spindle 3 at 100 rpm at 25° C. for 1 minute.

TABLE 5 pH values for samples at −10° C. and −30° C. over time and after slow thaw

| Sample | Initial pH | pH @ −10° C./ 1 day (Δ) | pH @ −10° C./ 3 day (Δ) | pH @ −10° C./ 5 day (Δ) | pH @ −30° C./ 1 day (Δ) | pH @ −30° C./ 3 day (Δ) | pH @ −30° C./ 5 day (Δ) | pH @ −30° C./ slow (Δ) |
|---|---|---|---|---|---|---|---|---|
| 1 | 4.9 | 4.9 (0.02) | 4.9 (0.01) | 4.9 (0) | 4.9 (−0.03) | 5.0 (−0.08) | 4.9 (0.1) | 4.9 (0) |
| 2 | 5.0 | 5.0 (0.01) | 5.0 (0.02) | 5.0 (−0.02) | 5.0 (−0.01) | 5.0 (0.03) | 5.0 (−0.03) | 5.0 (0.01) |
| 3 | 4.9 | 4.9 (0.03) | 4.9 (−0.04) | 4.9 (0.01) | 4.9 (−0.01) | 4.9 (0.01) | 4.9 (0) | 5.0 (−0.03) |
| 4 | 5.0 | 5.0 (0.04) | 5.0 (−0.02) | 5.0 (0) | 5.0 (0) | 5.0 (0) | 5.0 (0) | 5.0 (0.01) |
| 5 | 5.0 | 4.9 (0.05) | 5.0 (−0.01) | 4.9 (0.02) | 5.0 (−0.02) | 4.9 (0.01) | 5.0 (−0.02) | 5.0 (0.01) |
| 6 | 5.0 | 4.9 (0.01) | 4.9 (0) | 4.9 (0.03) | 4.9 (−0.01) | 4.9 (−0.01) | 4.9 (0) | 4.9 (0) |
| 7 | 4.9 | 4.9 (−0.05) | 4.9 (0.02) | 4.9 (−0.01) | 4.9 (0.01) | 4.9 (−0.01) | 4.9 (0.01) | 4.9 (0.02) |
| 8 | 5.0 | 4.9 (0.05) | 5.0 (−0.04) | 5.0 (0.01) | 5.0 (−0.02) | 5.0 (0.01) | 5.0 (0) | 5.0 (−0.01) |
| 9 | 5.0 | 4.8 (0.13) | 4.8 (0.01) | 4.8 (0.02) | 4.9 (−0.14) | 4.9 (0.09) | 4.9 (−0.04) | 4.9 (0.04) |
| 10 | 4.9 | 4.8 (0.14) | 4.9 (−0.08) | 4.8 (0.06) | 4.9 (−0.04) | 4.9 (−0.03) | 4.8 (0.04) | 4.8 (0.01) |
| 11 | 4.9 | 4.8 (0.14) | 4.9 (−0.05) | 4.9 (−0.01) | 4.8 (0.05) | 4.9 (−0.04) | 4.9 (−0.01) | 4.9 (0) |
| 12 | 4.9 | 4.9 (0.01) | 4.9 (−0.03) | 4.9 (0.05) | 4.9 (0.02) | 4.9 (−0.05) | 4.9 (0.04) | 4.9 (−0.03) |
| 13 | 4.9 | 4.9 (0.03) | 4.8 (0.04) | 4.9 (−0.04) | 4.9 (−0.01) | 4.9 (−0.01) | 4.9 (0.03) | 4.8 (0.01) |
| 14 | 4.9 | 4.8 (0.06) | 4.8 (0.07) | 4.8 (−0.07) | 4.8 (0.04) | 4.8 (−0.04) | 4.8 (0.02) | 4.8 (−0.01) |
| 15 | 5.0 | 4.9 (0.12) | 4.9 (−0.01) | 4.9 (0.02) | 4.9 (−0.02) | 4.9 (−0.03) | 4.9 (0.05) | 4.9 (−0.01) |
| 16 | 5.0 | 4.9 (0.12) | 4.9 (−0.03) | 4.9 (0.04) | 4.9 (−0.07) | 4.9 (0.04) | 4.9 (−0.05) | 4.9 (0.06) |
| 17 | 4.9 | 4.9 (0.04) | 4.8 (0.08) | 4.8 (−0.01) | 4.8 (−0.03) | 4.9 (−0.09) | 4.9 (0.04) | 4.8 (0.03) |

TABLE 6

Viscosity values for samples at −10° C. and −30° C. over time and after slow thaw

| Sample | Initial viscosity | Visc @ −10° C./1 day | Visc @ −10° C./3 days | Visc @ −10° C./5 days | Visc @ −30° C./1 day | Visc @ −30° C./3 days | Visc @ −30° C./5 days | Visc @ −30° C./ slow |
|---|---|---|---|---|---|---|---|---|
| 1 | 26 | 23 | 22 | 20 | 20 | 21 | 20 | 20 |
| 2 | 37 | 30 | 29 | 25 | 28 | 25 | 23 | 25 |

TABLE 6-continued

Viscosity values for samples at −10° C. and −30° C. over time and after slow thaw

| Sample | Initial viscosity | Visc @ −10° C./1 day | Visc @ −10° C./3 days | Visc @ −10° C./5 days | Visc @ −30° C./1 day | Visc @ −30° C./3 days | Visc @ −30° C./5 days | Visc @ −30° C./ slow |
|---|---|---|---|---|---|---|---|---|
| 3 | 19 | 18 | 16 | 15 | 18 | 16 | 16 | 16 |
| 4 | 40 | 34 | 34 | 25 | 29 | 25 | 23 | 26 |
| 5 | 31 | 31 | 24 | 23 | 31 | 22 | 21 | 24 |
| 6 | 30 | 26 | 22 | 22 | 23 | 21 | 21 | 22 |
| 7 | 27 | 22 | 21 | 21 | 21 | 21 | 18 | 19 |
| 8 | 24 | 21 | 19 | 18 | 19 | 19 | 17 | 17 |
| 9 | 27 | 29 | 23 | 22 | 28 | 27 | 20 | 24 |
| 10 | 21 | 22 | 19 | 20 | 21 | 17 | 18 | 18 |
| 11 | 29 | 25 | 25 | 23 | 24 | 23 | 22 | 28 |
| 12 | 38 | 33 | 31 | 26 | 30 | 31 | 28 | 30 |
| 13 | 24 | 25 | 21 | 20 | 21 | 22 | 18 | 24 |
| 14 | 21 | 21 | 20 | 16 | 21 | 20 | 18 | 19 |
| 15 | 29 | 27 | 22 | 25 | 26 | 23 | 20 | 27 |
| 16 | 27 | 27 | 28 | 21 | 23 | 22 | 21 | 24 |
| 17 | 20 | 20 | 17 | 16 | 20 | 17 | 17 | 18 |

The results of the study demonstrate that the samples tested are robust, as the responses fell within the targeted specifications in spite of the +/−10% ingredient variations. There was very little difference in the pH between runs over time and aging conditions. Although the viscosity results were highly correlated for all runs and aging conditions, the viscosity values remained within the targeted range of the samples.

The responses of the variables were further analyzed for main effects and interactions. Specifically, the pH did not vary between runs or aging conditions during the course of the study with the maximum difference in pH being only 0.1 pH units from the initial value. All of the viscosity responses were highly correlated with sodium laureth sulfate and cocoamidopropyl betaine being the most significant variables. The other main effects and interactions were not significant with regards to the viscosity.

A qualitative appearance analysis was completed on the samples during the freeze/thaw aging process. It was observed that there were no issues with precipitation and/or haziness during the −10° C. freeze/thaw cycle. However, precipitation and/or haziness was observed on all samples except Sample 14 and Sample 16 during the −30° C. freeze/thaw cycle.

Example 4

Two sample liquid body wash compositions were prepared, one comprising 0.5% PEG-60 hydrogenated castor oil and one comprising 1% PEG-60 hydrogenated castor oil. The color and appearance of the compositions were measured for clarity and haziness after one, two, and three freeze-thaw cycles at −10° C.; after one, two, and three freeze-thaw cycles at −30° C.; and after a slow freeze-thaw cycle from −30° C. to −10° C. to 4° C. to 25° C., as described above in Example 3. Both compositions were initially clear liquids, with no indication of cloudiness and/or haziness. A composition was determined to pass the freeze-thaw test if the composition remained clear and non-hazy both before and after the freeze-thaw cycle. Likewise, if the composition became cloudy and/or hazy after the freeze-thaw cycle, it was determined to have failed the freeze-thaw test. The results are shown below in Table 7.

TABLE 7

Freeze/thaw stability analysis

| % weight of PEG-60 hydrogenated castor oil in composition | Freeze/thaw conditions | Color/appearance of composition after freeze/thaw cycle |
|---|---|---|
| 0.5% | Cycle #1; −10° C. | Clear liquid; pass |
|  | Cycle #2; −10° C. | Clear liquid; pass |
|  | Cycle #3; −10° C. | Clear liquid; pass |
|  | Cycle #1; −30° C. | Hazy/cloudy liquid; fail |
|  | Cycle #2; −30° C. | Hazy/cloudy liquid; fail |
|  | Cycle #3; −30° C. | Hazy/cloudy liquid; fail |
|  | Slow thaw | Clear liquid; pass |
| 1% | Cycle #1; −10° C. | Clear liquid; pass |
|  | Cycle #2; −10° C. | Clear liquid; pass |
|  | Cycle #3; −10° C. | Clear liquid; pass |
|  | Cycle #1; −30° C. | Clear liquid; pass |
|  | Cycle #2; −30° C. | Clear liquid; pass |
|  | Cycle #3; −30° C. | Clear liquid; pass |
|  | Slow thaw | Clear liquid; pass |

As shown in Table 7, the composition comprising 1% PEG-60 hydrogenated castor oil passed all of the stability testing conditions, showing a clear liquid with no indication of cloudiness and/or haziness after any of the freeze-thaw conditions.

Example 5

Two liquid cleansing compositions (Sample 418 and Sample #19), each of which comprised 0.5% PEG-60 hydrogenated castor oil, were prepared and a study was conducted to measure their aging stability over time and under various conditions. The samples contained different colorants and/or fragrances. Both Sample #18 and Sample #19 were initially clear liquids. Their appearance was determined to pass the aging stability study if the composition's appearance remained clear and not cloudy and/or hazy after the aging conditions were applied. The following aging conditions were varied: temperature, time, relative humidity (RH), fluorescence exposure, and window/sun/LV exposure. The results are shown below in Tables 8 and 9.

TABLE 8

Aging stability study for Sample #18
(0.5% PEG-60 hydrogenated castor oil)

| Condition | Time | # of times a sample was drawn | pH | Color, odor, and appearance | Viscosity (mPas) |
|---|---|---|---|---|---|
| −10° C. | 1 day | 1 | 4.98 | Pass | 28 |
| −10° C. | 3 days | 1 | 4.99 | Pass | 27 |
| −10° C. | 5 days | 1 | 4.99 | Pass | 27 |
| −30° C. | 1 day | 1 | 4.99 | Pass | 29 |
| −30° C. | 3 days | 1 | 4.99 | Pass | 29 |
| −30° C. | 5 days | 1 | 5.02 | Pass | 27 |
| −30° C./slow thaw | 5 days | 1 | 5.02 | Pass | 24 |
| 25° C./60% RH | 4 weeks | 8 | 4.93 | Pass | 29 |
| 25° C./60% RH | 8 weeks | 2 | 5.04 | Pass | 27 |
| 25° C./60% RH | 13 weeks | 2 | 4.89 | Pass | 30 |
| 40° C./75% RH | 4 weeks | 2 | 4.91 | Pass | 29 |
| 40° C./75% RH | 8 weeks | 3 | 4.97 | Pass | 30 |
| 40° C./75% RH | 13 weeks | 2 | 4.95 | Pass | 32 |
| 49° C. | 4 weeks | 7 | 4.90 | Pass | 31 |
| 4° C. | 4 weeks | 1 | 4.95 | Pass | 28 |
| 4° C. | 8 weeks | 1 | 5.03 | Pass | 27 |
| 4° C. | 13 weeks | 1 | 4.96 | Pass | 29 |
| Fluorescence | 4 weeks | 1 | 4.95 | Pass | 30 |
| Window/sun/UV | 4 weeks | 1 | 4.98 | Pass | 29 |

TABLE 9

Aging stability study for Sample #19
(0.5% PEG-60 hydrogenated castor oil)

| Condition | Time | # of times a sample was drawn | pH | Color, odor, and appearance | Viscosity (mPas) |
|---|---|---|---|---|---|
| −10° C. | 1 day | 1 | 5.02 | Pass | 27 |
| −10° C. | 3 days | 1 | 4.99 | Pass | 23 |
| −10° C. | 5 days | 1 | 5.00 | Pass | 26 |
| −30° C. | 1 day | 1 | 5.01 | Pass | 21 |
| −30° C. | 3 days | 1 | 4.99 | Pass | 25 |
| −30° C. | 5 days | 1 | 4.99 | Pass | 28 |
| −30° C./slow thaw | 5 days | 1 | 4.98 | Pass | 21 |
| 25° C./60% RH | 4 weeks | 8 | 5.00 | Pass | 29 |
| 25° C./60% RH | 8 weeks | 2 | 4.96 | Pass | 30 |
| 25° C./60% RH | 13 weeks | 2 | 4.99 | Pass | 30 |
| 40° C./75% RH | 4 weeks | 2 | 4.96 | Pass | 30 |
| 40° C./75% RH | 8 weeks | 3 | 4.94 | Pass | 29 |
| 40° C./75% RH | 13 weeks | 2 | 4.90 | Pass | 33 |
| 49° C. | 4 weeks | 7 | 4.96 | Pass | 32 |
| 4° C. | 4 weeks | 1 | 5.01 | Pass | 29 |
| 4° C. | 8 weeks | 1 | 4.98 | Pass | 27 |
| 4° C. | 13 weeks | 1 | 4.99 | Pass | 30 |
| Fluorescence | 4 weeks | 1 | 5.00 | Pass | 30 |
| Window/sun/UV | 4 weeks | 1 | 4.99 | Pass | 30 |

Sample #18 was further tested at 25° C. with 4 separate pulls. The average pH of the sample was 5.01 with a specific gravity measured at 1.03 and a viscosity of 30 mPas. No flash point was detected at tests up to 200° F.

The Micro Robustness Index (MRI) of Sample #18 was measured. The MRI is used as a quantitative measure of a composition's ability to withstand microbial challenge. The MRI is the result from a challenge test assessing the antimicrobial efficacy of a composition against a pool of microorganisms. Samples are challenged with an inoculum of bacteria, and aliquots are tested to measure the log reduction of bacteria. Using these data, the area under the curve (AUC) is calculated and then converted into the MRI; the higher the MRI, the greater the microrobustness of the tested composition. A single micro-robustness challenge yielded a micro-robustness index (MRI) of 1.36 for Sample #18.

Sample #19 was also further tested at 25° C. with 4 separate sample draws. The average pH of the sample was 5.00 with a specific gravity measured at 1.03 and a viscosity of 28 mPas. No flash point was detected at tests up to 200° F. A single micro-robustness challenge yielded an MRI of 1.4.

The results of the aging study demonstrate that both Sample #18 and #19 remained stable under all of the aging conditions tested.

While the disclosure has been described with respect to specific examples including presently preferred modes of carrying out the disclosure, those skilled in the art will appreciate that there are numerous variations and permutations of the above-described systems and techniques. It is to be understood that other embodiments may be utilized and structural and functional modifications may be made without departing from the scope of the present disclosure. Thus, the scope of the disclosure should be construed broadly as set forth in the appended claims.

What is claimed is:

1. A liquid cleansing composition comprising:
    a) a foam booster comprising ethoxylated hydrogenated castor oil present in an amount ranging from 0.45% to 1% based on the total weight of the composition;
    b) castor oil maleate;
    c) glycerin; and
    d) at least one surfactant,
    wherein the composition is clear and the pH of the composition is less than about
    wherein the at least one surfactant comprises sodium lauryl ether sulfate and cocoamidopropyl betaine; and
    wherein the ethoxylated hydrogenated castor oil is PEG-60 hydrogenated castor oil.

2. The composition of claim 1, wherein the composition has a viscosity ranging from about 1 to about 100 mPas (cps).

3. The composition of claim 1, wherein the ethoxylated hydrogenated castor oil is present in an amount of 0.45%, 0.5%, 0.55% or 1%, by weight of the composition.

4. The composition of claim 1, wherein the composition is substantially free of any additional foam booster.

5. The composition of claim 1, further comprising PEG-120 methyl glucose dioleate.

6. The composition of claim 5, wherein the PEG-120 methyl glucose dioleate is present in an amount ranging from about 0.01% to about 0.5% by weight of the composition.

7. The composition of claim 1, further comprising PEG-7 glyceryl cocoate.

8. The composition of claim 1, wherein the castor oil maleate is present in an amount ranging from about 0.1% to about 1% by weight based on the total weight of the composition.

9. The composition of claim 1, comprising 0.45-0.55% by weight PEG-60 hydrogenated castor oil, 0.27-0.33% by weight maleated castor oil, 3.08-3.77% by weight glycerin, 9.78-11.95% by weight sodium laureth sulfate, 5.4-6.6% by weight CAP betaine, and one or more optional ingredients selected from 0.05-0.5% by weight tetrasodium EDTA, 0.20% by weight PEG-7 glyceryl cocoate, 0.15% by weight PEG-120 methyl glucose dioleate, 0.55% by weight citric acid, 0.05-0.5% by weight sodium benzoate, 0.05-0.5% by weight sodium salicylate, colorants, and fragrances.

10. The composition of claim 1, wherein the composition is a body wash.

11. The composition of claim 1, wherein the composition is a hand soap.

12. The composition of claim 1, wherein the composition remains clear after the composition has been frozen at −10° C. for at least one day and then thawed.

13. The composition of claim 1, wherein the composition remains clear after the composition has been frozen at −30° C. for at least one day and then thawed.

14. A method of making a clear liquid cleansing composition, the method comprising:
   mixing maleated castor oil and at least one fragrance to form a first mixture;
   mixing a foam booster comprising PEG-60 hydrogenated castor oil present in an amount ranging from 0.45% to 1% by weight based on the total weight of the liquid cleansing composition, glycerin, and at least one surfactant comprising sodium lauryl ether sulfate and cocoamidopropyl betaine to form a second mixture;
   combining the first mixture and the second mixture to form the liquid cleansing composition; and
   adjusting the pH of the liquid cleansing composition to a pH of less than about 7.

15. The method of claim 14, wherein the at least one fragrance is present in an amount of about 1% by weight based on the total weight of the liquid cleansing composition.

* * * * *

UNITED STATES PATENT AND TRADEMARK OFFICE
CERTIFICATE OF CORRECTION

PATENT NO. : 12,023,404 B2
APPLICATION NO. : 16/957425
DATED : July 2, 2024
INVENTOR(S) : Nadine Dewdney et al.

It is certified that error appears in the above-identified patent and that said Letters Patent is hereby corrected as shown below:

In the Specification

In Column 5, Line 23, after "about 6", delete "?".
In Column 10, Line 14, delete "025%", and insert -- 0.25% --, therefor.

Signed and Sealed this
Twentieth Day of August, 2024

*Katherine Kelly Vidal*

Katherine Kelly Vidal
*Director of the United States Patent and Trademark Office*